United States Patent [19]

Slavin

[11] Patent Number: 4,483,346

[45] Date of Patent: Nov. 20, 1984

[54] ELECTROCARDIOGRAPH WITH DIGITALLY-PRINTING WAVEFORM DISPLAY

[75] Inventor: Martin J. Slavin, Dix Hills, N.Y.

[73] Assignee: Intech Systems Corp., Hauppauge, N.Y.

[21] Appl. No.: 526,260

[22] Filed: Aug. 25, 1983

[51] Int. Cl.³ .............................................. A61B 5/04
[52] U.S. Cl. ............................... 128/710; 346/33 ME
[58] Field of Search ............... 128/695, 696, 702–704, 128/709–712, 715; 346/33 ME; 364/417

[56] References Cited

U.S. PATENT DOCUMENTS

| | | | |
|---|---|---|---|
| 3,171,406 | 9/1981 | Baum et al. | 128/715 |
| 3,773,033 | 11/1973 | Rodbard et al. | 128/709 |
| 3,868,948 | 3/1975 | Graetz | 128/709 |
| 3,990,435 | 11/1976 | Murphy | 128/715 |
| 4,098,267 | 7/1978 | Stein et al. | 128/712 |
| 4,115,864 | 9/1978 | Vick et al. | 128/702 |
| 4,254,302 | 3/1981 | Walshe | 128/715 |
| 4,256,888 | 2/1981 | Grosskopf | 128/702 |
| 4,301,809 | 11/1981 | Pinchak | 128/695 |
| 4,331,159 | 5/1982 | Bax et al. | 128/710 |
| 4,339,800 | 7/1982 | Woods | 128/702 |
| 4,364,397 | 12/1982 | Citron et al. | 128/710 |

OTHER PUBLICATIONS

Adler et al., "Medical Instrumentation", vol. 13, No. 4, Jul.-Aug. 1979, pp. 216-217.

Primary Examiner—William E. Kamm
Attorney, Agent, or Firm—Blum, Kaplan, Friedman, Silberman & Beran

[57] ABSTRACT

An electrocardiograph included microprocessor control of signals not only from conventional electrocardiograph electrodes but also from a phonocardiographic pickup. The signals are multiplexed, converted to digital representations for processing and are displayed on a printer. Keyboard control of the microprocessor and both analog signal and modem outputs are provided.

20 Claims, 3 Drawing Figures

ELECTROCARDIOGRAPH WITH DIGITALLY-PRINTING WAVEFORM DISPLAY

BACKGROUND OF THE INVENTION

This invention relates generally to a cardiograph of the type used to provide a record of data from conventional electrocardiograph sensors which are applied to a patient's body and more particularly to a small, hand held, battery powered miniature phono- and electrocardiograph which may be conveniently carried by doctors, nurses, interns, technicians and emergency service personnel. Conventional EKG machines are used under controlled conditions wherein the patient is carefully prepared for the measurements which are to be made. The machines are generally bulky and expensive and for both reasons are not considered portable such that a doctor would transport them in his normal rounds, nor would these instruments be practical for transport by nurses, technicians and the like. Thus the use of EKG machines has been limited although the permanent record which these machines provide of a patients condition at a given moment of time is an invaluable tool to the practioner.

Another disadvantage of conventional machines outputting a cardiogram is the size and delicateness of the printer which is required to produce a substantially instantaneous analog representation of the EKG signals as they are detected. The ability of the recording pen to accurately follow the inputted electrical driving signals leaves room for improvement and the use of an oscilloscope, while accurately following the electrical signals, provides no permanent record unless supplementary equipment for photographic recording is provided. Thus the complexity of such devices is compounded and portability enabling on-site utility is further limited.

Further, it would be medically useful to provide a permanent record of a signal representative of the audible output of a stethoscope, so as to provide a permanent record, and to permit comparison with an electrocardiogram of the patient.

What is needed is a miniature phono- and electrocardiograph which is small, lightweight and therefore portable, and provides an accurate, permanent record of EKG and phono inputs as from a stethoscope.

SUMMARY OF THE INVENTION

Generally speaking, in accordance with the invention, a miniature phono- and electrocardiograph is provided especially suitable for hand held portable operation. The miniature phono- and electrocardiograph is hand held and battery powered. The device includes a digitally driven miniature printer capable of simultaneously printing data received from at least two body sensors. Signals from conventional EKG electrodes or from a phono output of a stethoscope such as the differential stethoscope as disclosed in my co-pending application Ser. No. 366,516, filed Apr. 8, 1982, are selected by multiplexing in accordance with machine instructions provided by the user. The selected multiplex signals are converted from analog to digital format and stored in a random access memory all under control of a microprocessor. Substantially concurrently with the input of data to the random access memory, said data is read out under control of the microprocessor and input to the digitally driven printer to provide a printed record of the original EKG inputs. The speed of reading data from the memory to drive the printer is slower than the speed of writing data into memory from the sensors.

Outputs are provided on the device for interfacing with an oscilloscope and with a modem for transmission of the digitized data by telephone or other data transmission means for analysis at a remote location. A keyboard allows the user to select for printout among the various EKG electrodes and the phono input from the stethoscope which may be simultaneously connected to the miniature phono- and electrocardiograph. The user also inputs identification data by means of the keyboard, for example, the patient's name, the operator's name, date, time, and the like and identification of the selected channels which are being recorded. The printer prints this information on the record with the printout of the actual EKG and phono data. Date and time information can be automatically printed from an internal timer in the device. The keyboard may also permit selection of the gain, time base, number of beats to be recorded, special filters and other output signal-defining features, by applying control signals to the microprocessor. A display such as a liquid crystal display, indicates the identification data as it is input by the user to permit checking for accuracy, and also displays instructions for the user and requests for information from the user as required for a complete record, under control of the microprocessor and using data stored in a read only memory. A rechargable battery powers all circuits.

Accordingly, it is an object of this invention to provide an improved miniature phono- and electrocardiograph which is small and can be hand held.

Another object of this invention is to provide an improved miniature phono- and electrocardiograph which is battery powered and can be used in the field under uncontrolled conditions.

A further object of this invention is to provide an improved miniature phono- and electrocardiograph which can select for printing among a plurality of EKG inputs and a phono input from a stethoscope.

A still further object of the invention is to provide a portable electrocardiograph incorporating a digitally controlled printer which prints at a rate slower than the rate of input of the EKG signals into the device.

Still another object of this invention is to provide an improved miniature phono- and electrocardiograph which provides a permanent, accurate printed record of the recorded data, including identifying information.

Yet another object of this invention is to provide an improved miniature phono- and electrocardiograph which provides ongoing instructions and requests information from the user as required for a complete and accurate recording of data.

Still other objects of the invention will in part be obvious and will in part be apparent from the specification.

The invention accordingly comprises the features of construction, combination of elements, and arrangements of parts which will be exemplified in the construction hereinafter set forth, in the scope of the invention and will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
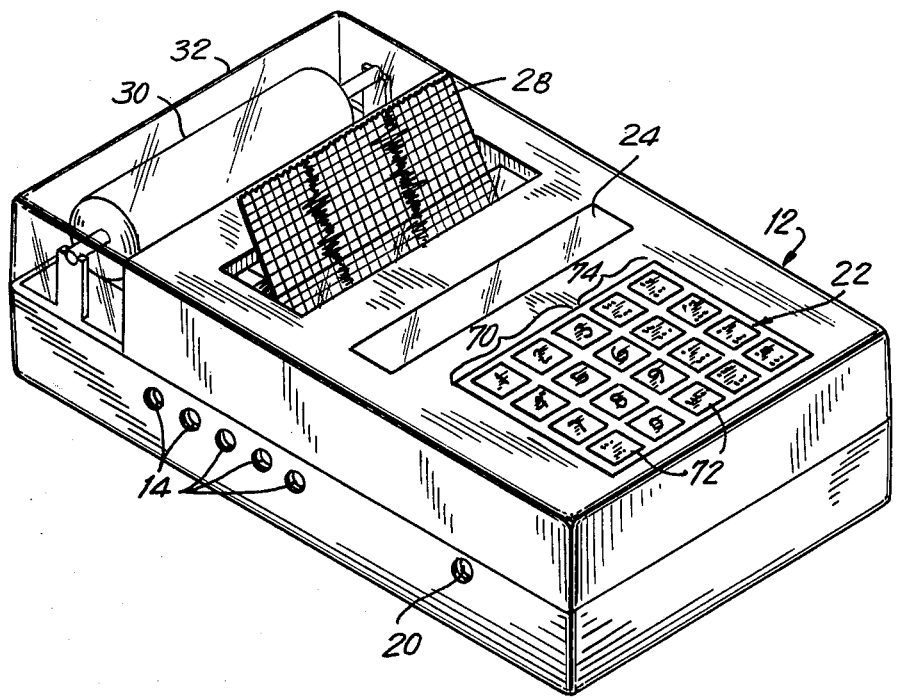
FIG. 1 is a top, left, front perspective view of a miniature phono- and electrocardiograph in accordance with the invention.
Figure 2:
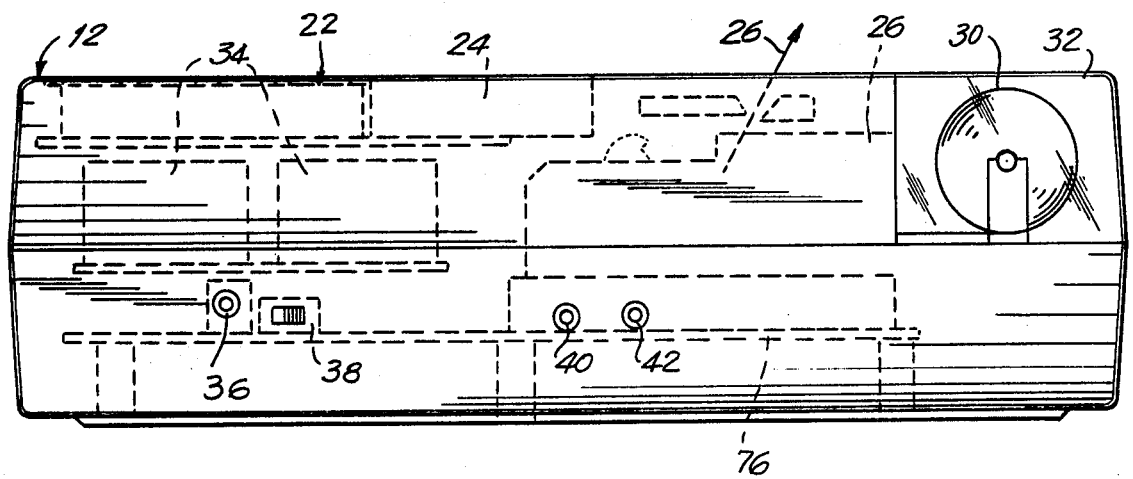
FIG. 2 is a right side view of the electrocardiograph of FIG. 1.

With reference to the Figures, the phono- and electrocardiograph 10 in accordance with the invention includes a case 12 having on the left side surface thereof a plurality of input jacks 14 for connection with EKG electrodes which may be applied in the conventional manner to a patient for the purpose of producing cardiograms. A jack 20 provides for input of the electrical (phono) output of a stethoscope having an electroacoustic transducer such as the differential stethoscope of the type disclosed in my co-pending U.S. application Ser. No. 366,516, filed Apr. 8, 1982 now U.S. Pat. No. 4,438,772. This input provides an analog signal representative of the patient's heartbeat and heart sounds.

The phono- and electrocardiograph 10 also includes a keyboard 22 on the top surface thereof for inputting alpha-numeric information as explained more fully hereinafter, and a liquid crystal display 24 on the top surface thereof for providing a visual indication of the inputs to the keyboard 22 and other information. A printer 26 mounted within the case 12 prints on a recording sheet 28 which is supplied to the printer 26 from a roll 30, retained within the case 12 and made visible by a transparent removable cover 32.

The phono- and electrocardiograph 10 includes battery packs 34 which are chargeable by means of an input jack 36 located on the right side surface of the case 12 opposite from the EKG input jacks 14 and phono input jack 20. An ON-OFF switch 38, which controls application of battery power to the other electrical elements of the phono- and electrocardiograph 10 is also located on the side surface of the case 12. A first output jack 40 provides an analog output of any selected signal which is being input at the jacks 14, 20 for the purpose of applying the signal to another cardiograph device, or to an oscilloscope for display. A second output jack 42 can selectively provide digitized, multiplexed data output signals representative of one or more of the inputs to jacks 14, 20 in a format suitable for data transmission. The phono- and electrocardiograph 10 includes a modem 43 coupled to output jack 42 for transmitting the data by telephone or for transmitting the recorded data to temporary or permanent storage externally of the phono- and electrocardiograph 10 of this invention.

Figure 3:
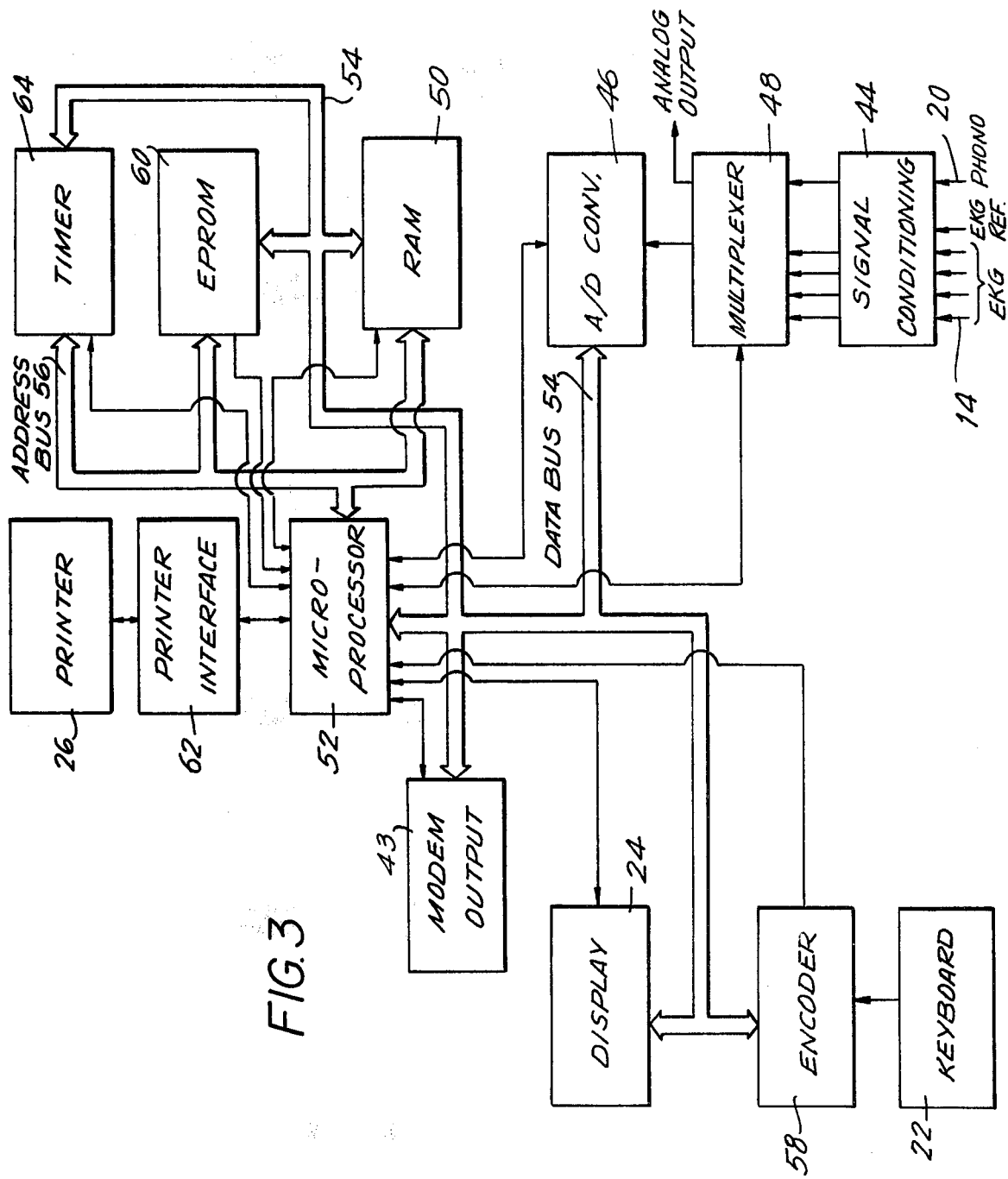
FIG. 3 is a functional block diagram of a miniature phono- and electrocardiograph in accordance with the invention.

In the embodiment depicted, five EKG inputs are provided, one, for example the right leg input, serving as a reference signal in a conventional manner. Additional EKG inputs can be provided if desired. As best seen in FIG. 3, the EKG or phono signals received at the jacks 14, 20 are input to signal conditioning circuits 44 where the signals are normalized by adjusting the amplitudes to provide maximum peaks at full scale in the data storage and printing process. The analog inputs are then fed to an analog to digital converter 46 by way of a multiplexer 48. Multiplexer 48 operates under the direction of a microprocessor 52, which in turn is controlled by instructions from the user inputted through keyboard 22 or by instructions stored in a read only memory (EPROM 60) as more particularly described below. Multiplexer 48 includes microprocessor controlled switches which selectively direct the input signals from jacks 14, 20 to addition, subtraction, averaging and filter circuits to produce the desired combination of inputs which are more conventionally used in electrocardiographs, as well as such future combinations as may be desired. Thus, by way of example, among the combinations of signals frequently produced are the difference between the left arm (LA) and right arm (RA) inputs (denominated I), and the difference between the right arm input (RA) and the average of the left arm (LA) and left leg (LL) inputs (denominated AVR). The individual or combined inputs can be selectively passed through one/or more filters such as an artifacts filter adapted to filter out the effects of various electrical signals. One or more of the individual or combined inputs, after filtering if desired, is selected as directed by the multiprocessor for sampling and digitizing. The sampled digitized data of the selected inputs or combinations of inputs are stored in consecutive addresses of a random access memory 50 (RAM). If two signals are to be printed, displayed or transmitted, each memory address or consecutive memory addresses contains essentially contemporaneous samples of the two signals selected for printing, display or transmission. Since the sampling rate is selected to be very high as compared to the rate of the sampled signals, the sampled signal portions stored in RAM 50 provide an accurate representation of the desired signal, and where there are two such originals, they can be deemed to be contemporaneous. In one embodiment a sampling rate of about 2,000 per second is used.

Microprocessor 52 controls operation of the multiplexer 48, analog to digital converter 46, and RAM 50, including the selection of addresses in the RAM 50 for storage of the digitized data. The data from the analog to digital converter 46 is transmitted to the microprocessor 52 by way of a two-way data bus 54 which also provides data input to the RAM 50. An address bus 56, connects the microprocessor 52 to the RAM 50 allowing the microprocessor 52 to control address selection for storage of digitized signal data.

The microprocessor is adapted to process the sampled and digitized input data as instructed by the user by means of keyboard 22. Microprocessor 43 can be instructed by the user through keyboard 22 to adjust the gain of the input signals, to set the number of beats of the input signal to be recorded and to set the time base of the portion of the input signal to be recorded. Due to practical limitations in the size of RAM 50, only a limited number of beats of EKG signal or phono signal can be processed at each operation of the device. However, with provision of additional memory, additional beats can be stored. Time base may be adjusted by selecting the speed of feed of print medium 28. Gain can be expressed in terms of sensitivity, the number of millimeters of deflection on the print out per millivolts of input. Both time base and gain can be controlled continuously through the keyboard but in one embodiment, three pre-set choices for each are provided, selected by its user through the keyboard, and remaining unchanged from use to use until changed.

Numbers or instructions input by depressing keys on the keyboard 22 are encoded in an encoder 58 into signals suitable for transmission on common data bus 54. These encoded signals are translated into signals for driving the liquid crystal display or the printer by the microprocessor, using codes stored in the electrically programmable read only memory (EPROM) 60 in a conventional manner. Using the keys on the keyboard, the user may insert data identifying the equipment operator, the patient and channels or signals which are selected for printing. The phono- and electrocardiograph is user-friendly in that EPROM 60 includes instructions for the user, directing the user in the proper sequence of operations and requesting particular inputs from the user at the proper time such that these inputs may be stored in RAM 50 in the proper addresses selected by the microprocessor 52. The instructions from EPROM 60 to the user are in the form of instruction signals driving the display 24, alerting the user to his next operation or identification data input. The displayed instructions can be alpha-numeric. The microprocessor also displays the inputs inserted by the user to insure accuracy of inputs. The display can be of any form but is preferably by a liquid crystal display. If a dot matrix display is used, the sampled, digitized data could be displayed on display 24.

The printer 26 is of any conventional digitally driven type which provides a print head traversing on a carriage across the face of the print medium 28 or the traverse of the print medium laterally on a carriage relative to a print head and providing for feeding of the print medium 28 in a direction transverse to the motion of the carriage.

The signal data stored in the RAM 50 is input to the printer 26 from consecutive addresses in the order of storage, starting essentially simultaneously with data input. The data from the RAM 50 is read by the microprocessor and input to a printer interface 62 which drives the print head to print on the recording medium 28. Printing is effected when the carriage reaches the lateral position in its traverse across the medium corresponding to the digitized data stored in the memory address which has been read. The memory address is advanced in correlation with the motion of the print head across the print media, coordinated by the microprocessor 52 when data for each curve is stored in separate memory addresses. In an embodiment where each address contains data for both curves, the memory address is advanced after each carriage traverse and advancement of the print medium 28 relative to the print head. In both embodiments the print medium 28 is advanced upon completion of printing in each carriage traverse.

A timer circuit 64 also provides actual time and date information which may become a portion of the data stored in the RAM 50 for each operation of the device for later printing or such time and date information may be read from the timer circuit and directly transmitted to the printer for predating and is also printed out on the recording medium 28 when the recorded data signals are printed. Timer 64 may be set by operation of the keyboard under the control of the microprocessor. Address bus 56 is also connected to EPROM 60 and timer 64 to enable the microprocessor to access these devices for reading data from them and for setting the timer. Data bus 54 and address bus 56 are preferably common to a plurality of circuit elements as shown in FIG. 3 and are operated as shared, multiplexed buses to minimize cost and size.

The printer 26 prints a segment (a dot or line) of each of the one or two selected curves on the recording medium 28 in each traverse of the print head carriage in correspondence with the two data points which are stored in RAM 50. The printer may be of any digitally driven type, for example, a pen printer (where the pen is selectively engaged and lifted off the paper), wire dot printer, an ink jet printer, a thermal printer operating with sensitized paper, etc. In the case of a dot printer, if two curves are to be printed, two dots, one from each data signal, are printed in each traverse of the carriage. With a pen printer, for example, a dot or line portion is printed for each curve of the data signals in each traverse. At the beginning or end of printing of the stored data signals, the identifying data and time and date information are printed on the recording medium 28. For the identification, time and date data, the number of dots or line portions printed in each traverse depends upon the data to be printed. Whereas the data is input to the RAM memory 50 from the EKG terminals 40 and phono terminal 20 at a high sample rate and for a period of time determined by the capacity of the memory 50 and the desired duration of signal input, the rate of reading data from the RAM 50 and driving of said printer 26, is selected for optimum operation of the printer 26. Thus, the rate of data read out and printing is much lower than the data write-in rate. Therefore, printing is completed only after a time lag following completion of data input to the RAM 50, although printing begins substantially concurrently with the input of signal data to the RAM 50. The multiplexing of the addresses and data buses permits data input and printing to occur simultaneously.

Because read out of data from the RAM 50 is timed to accommodate the capabilities of the printer 26, a small, lowerspeed digitally driven printer may be used in this device as compared with the analog graphing mechanisms used in the electrocardiograph devices of the prior art. Because the carriage of the printer moves at a predetermined rate across the print medium 28 regardless of the magnitude of the signal data to be recorded, a printer operating in this fashion is extremely accurate and does not experience the deficiencies of conventional electromechanial pen-type devices which respond to analog signals input thereto and suffer deficiencies resulting from the mass of the pen and its carriage. Printers which operate at lower speeds are simpler in construction and accordingly, lower in cost and higher in reliability. Thus, by storing the input signal data in the memory 50 at a rapid rate sufficient to assure a large data accumulation and accuracy of the printed output, the deficiencies of the prior art are overcome, and a phono- and electrocardiograph which is sufficiently small so as to be portable and battery powered. A permanent record is provided without cumbersome set up procedures in the form of a cardiogram which is extremely accurate and permanently identified so as to avoid loss or misapplication.

It should be readily understood that the duration of sampling, that is, the amount of data which is stored temporarily for printout depends upon the size of the memory 50. The number of curves which are reproduced in one printing sequence can be varied depending upon the size of the RAM memory 50 and the degree of multiplexing which is provided. It should also be understood that a circulating memory may be used to store the data such that the content of a memory address is erased immediately after read out of that address and new data may subsequently be stored in the same memory address, thereby extending the amount of data which can be processed before the memory becomes "full".

It should also be understood that in alternative embodiments the incoming signals which had been conditioned can be printed out on the recording medium 28 with ordinate markings indicating the true scale of the signals.

In operation, the operator turns the unit on by operation of the switch 38 and follows the instructions provided on the liquid crystal display 24, making inputs by way of the keyboard 22 and connecting the sensor leads to the proper jack terminals 14, 20. The operator makes further inputs as requested by the unit to identify himself and the patient, to select the output for print out, and to input the date and time unless provision has been made for the microprocessor 52 to accomplish this task automatically using data from the timer circuits 64.

In response to an instruction to begin data collection appearing on the liquid crystal display 24, and by operating the keyboard 22 in response thereto, the incoming signals are allowed to enter the signal conditioning circuits 44 for processing as described above. Substantially concurrently, the printer commences operation, printing out the selected signal inputs as curves as the print media 28 moves out of the printer 26.

In one embodiment, ten of the keys of keyboard 22 in group 70 are used for numeric inputs. The remaining keys 72, 74, as well as the number keys in appropriate sequence can be used to initiate functions such as timer set, setting of number of beats, setting of gain, setting of time base, setting of patient or user codes, calibration, inserting of artifacts filter, reset or the like. Each key can perform more than one function depending on the setting of other keys. The device may function, either by selection or program in several modes. First, the device can automatically and sequentially produce a preselected series of single graphical printouts, each representative of a separate phono- or electrocardiograph output. Second, selected ones of the outputs can be printed. Third, two selected outputs such as a phono- and an electrocardiograph output can be printed simultaneously, side by side. By selection of the printer, even more of the outputs can be printed side by side, provided adequate memory capacity is provided.

Information can be printed before or after each curve or even next to each curve. In addition to curve identification, date, time and patient identification information, the degree of filtering, the time base, the gain (sensitivity) or other relevant information can be printed to provide the user with a full record of what is shown on the cardiogram.

It should also be understood that in an alternative embodiment of a phono- and electrocardiograph in accordance with the invention, printing does not commence until all input data signals have been stored in memory. Also each memory address may store data of more than one input jacks 14, 20.

In one embodiment, the case 12 is about 4.0 inches wide, 7.5 inches long and 1.6 inches thick. The phono- and electrocardiograph thus formed is readily portable and easily used.

It will thus be seen that the objects set forth above, among those made apparent from the preceding description, are efficiently attained and, since certain changes may be made in the above construction without departing from the spirit and scope of the invention, it is intended that all matter contained in the above description as shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An electrocardiograph for connection to sensors outputting analog electrical signals, comprising:
   at least one sensor outputting analog electrical signals;
   sampling means for selectively sensing at intervals at least one of such analog signals from at least one of said sensors;
   analog to digital conversion means for receiving said sampled analog signals and outputting digitized signals corresponding thereto;
   memory means including a plurality of addresses for storage of data therein;
   processor means for writing said consecutively sampled digitized signals representative of a predetermined duration of the at least one analog sensor output signal into said addresses of said memory means for storage therein in consecutive order;
   printer means for recording on a print medium in response to digital data input thereto, said processor means being further adapted to automatically read said stored date from said addresses in said memory means in said consecutive order and input said data to said printer means for printing a series of portions of a curve representative of the analog signal from said at least one sensor, said printer means being adapted to advance said print medium after printing each said curve portion, a cardiogram of said predetermined duration of said selectively sensed at least one analog signal being produced on said print medium extending in the direction of advance of said print medium, said processor means inputting said data to said printer during the time that data is written into said memory means but at a rate slower than the rate said data is written into said memory means.

2. An electrocardiograph as claimed in claim 1, including means for combining the outputs of at least two of said sensors so that at least one of said at least one sampled analog signals represents a combination of the outputs of at least two of said sensors.

3. An electrocardiograph as claimed in claim 1, including multiplexing means coupled intermediate said sensor outputs and said sampling means so that said processor means writes said digitized signals into and reads out said stored signals from said memory means for printing on a multiplexed basis.

4. An electrocardiograph as claimed in claim 1, wherein said sensors include at least one phono-cardiograph sensing element and a plurality of electrocardiograph sensing elements.

5. An electrocardiograph as claims 1, 2 or 4, wherein the quantity of said analog signals is at least two, each such analog signal being from at least one of said sensors and said sampling means includes multiplexing means, said analog sensor signals being input to said analog to digital conversion means on a multiplexed basis, at least two side by side cardiograms being simultaneously produced on said print medium, both cardiograms extending in the direction of advance of said print medium.

6. An electrocardiograph as claimed in claim 5, wherein said multiplexing means is controlled by said processor means.

7. An electrocardiograph as claimed in claim 6, and further comprising external selection means for selecting analog signals for data storage and print out from among the available analog signals.

8. An electrocardiograph as claimed in claim 7, wherein said selection means includes a keyboard operable by the user of said electrocardiograph, said analog signals being selected for print-out by keyboard inputs.

9. An electrocardiograph as claimed in claim 7, and further comprising display means, said display means visibly indicating which of said sensor signals have been selected for data storage and print out by operation of said selection means.

10. An electrocardiograph as claimed in claim 9, wherein said memory means further includes instructions stored in digital format in a portion of said addresses, said processor means causing said instructions to be decoded and visibly displayed alphanumerically by said display means, said instructions directing the user in correct operating procedures for said electrocardiograph.

11. An electrocardiograph as claimed in claim 10, wherein said displayed correct procedures specify at least in part operation of said external selection means by said user.

12. An electrocardiograph as claimed in claim 11, wherein said selection means includes a keyboard operable by the user of said electrocardiograph, said display means visibly verifying keyboard inputs by said user.

13. An electrocardiograph as claimed in claim 5, wherein said printer includes a print head mounted on a carriage for translation laterally across said print medium, and printer interface means for driving said head for printing, said print head being driven for printing on said medium whenever the lateral position of said carriage corresponds to said digitized data stored in and read from said memory means, said processor means directing read-out digitized data to said printer interface means.

14. An electrocardiograph as claimed in claim 13, wherein sampled digitized data from N analog signals is stored in said memory means and N cardiographs are printed substantially concurrently on said print medium when said digitized data is read out for printing.

15. An electrocardiograph as claimed in claim 1 and further comprising signal conditioning means coupled intermediate said at least one sensor and said sampling means for receiving said analog sensor signals and adjusting said signals for full scale print out on said print medium.

16. An electrocardiograph as claimed in claim 15, wherein said signal conditioning means is adapted to mix said analog signals from a plurality of said sensors.

17. An electrocardiograph as claimed in claim 16, wherein said signal conditioning means is further adapted to combine at least two of said analog sensor signals to output average and difference signals of said sensor signals to said sampling means.

18. An electrocardiograph as claimed in claim 1, wherein said memory means further stores operating instructions for said processor means in a portion of said addresses.

19. An electrocardiograph as claimed in claim 1, and further comprising an output terminal on said cardiograph, and means for selectively coupling at least one analog output signal from said sensors to said output terminal.

20. An electrocardiograph as claimed in claim 1, and further comprising an output terminal on said cardiograph, said processor means being further adapted to read digitized data from said memory means to said output terminal.

* * * * *